United States Patent [19]

Thaler

[11] Patent Number: 4,911,686
[45] Date of Patent: Mar. 27, 1990

[54] APPARATUS FOR REACTIVELY APPLYING ELECTRICAL ENERGY PULSES TO A LIVING BODY

[76] Inventor: Sheldon Thaler, 307 Wendover Dr., Princeton, Mercer County, N.J. 08540

[21] Appl. No.: 277,422

[22] Filed: Nov. 25, 1988

Related U.S. Application Data

[60] Continuation-in-part of Ser. No. 943,542, Dec. 17, 1986, abandoned, which is a division of Ser. No. 591,476, Mar. 20, 1984, Pat. No. 4,654,574, which is a division of Ser. No. 509,830, Jun. 20, 1983, abandoned.

[51] Int. Cl.$^4$ .............................................. A61N 1/40
[52] U.S. Cl. .................................... 600/14; 128/419 F
[58] Field of Search ........................... 600/943, 542, 14

[56] References Cited

U.S. PATENT DOCUMENTS

| | | | |
|---|---|---|---|
| 3,513,891 | 5/1970 | Smith et al. | 128/422 |
| 3,566,877 | 3/1971 | Smith et al. | 128/422 |
| 3,875,929 | 4/1975 | Grant | 128/653 |
| 4,428,366 | 1/1984 | Findl et al. | 128/1.5 |

FOREIGN PATENT DOCUMENTS 2707574  8/1978  Fed. Rep. of Germany ....... 128/1.3

Primary Examiner—Francis Jaworski
Attorney, Agent, or Firm—Hopgood, Calimafde, Kalil, Blaustein & Judlowe

[57] ABSTRACT

A device for therapeutic treatment of cells and tissues in a living body by non-invasively applying a developed field of pulsating electrical energy to a body site to stimulate repair or growth of bone structure at the body site containing electronic counters to control the desired number of pulses, the pulse repetition rate and the pulse duty cycle. A sensor may be used to detect the occurrence of an applied pulse and produce a signal to control the developed field and may also be used to feed a circuit which tests the developed field to determine if it is adequate for the intended purpose. As an added feature, a circuit is provided to recover a portion of the energy in the developed field, during its decline, to reduce power consumption and dissipation.

1 Claim, 6 Drawing Sheets

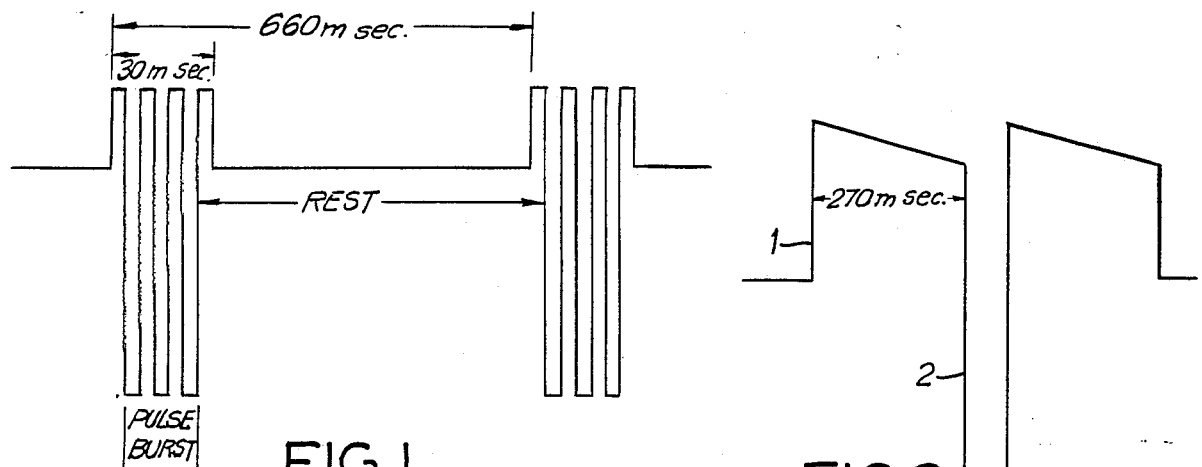
FIG.1
FIG.2
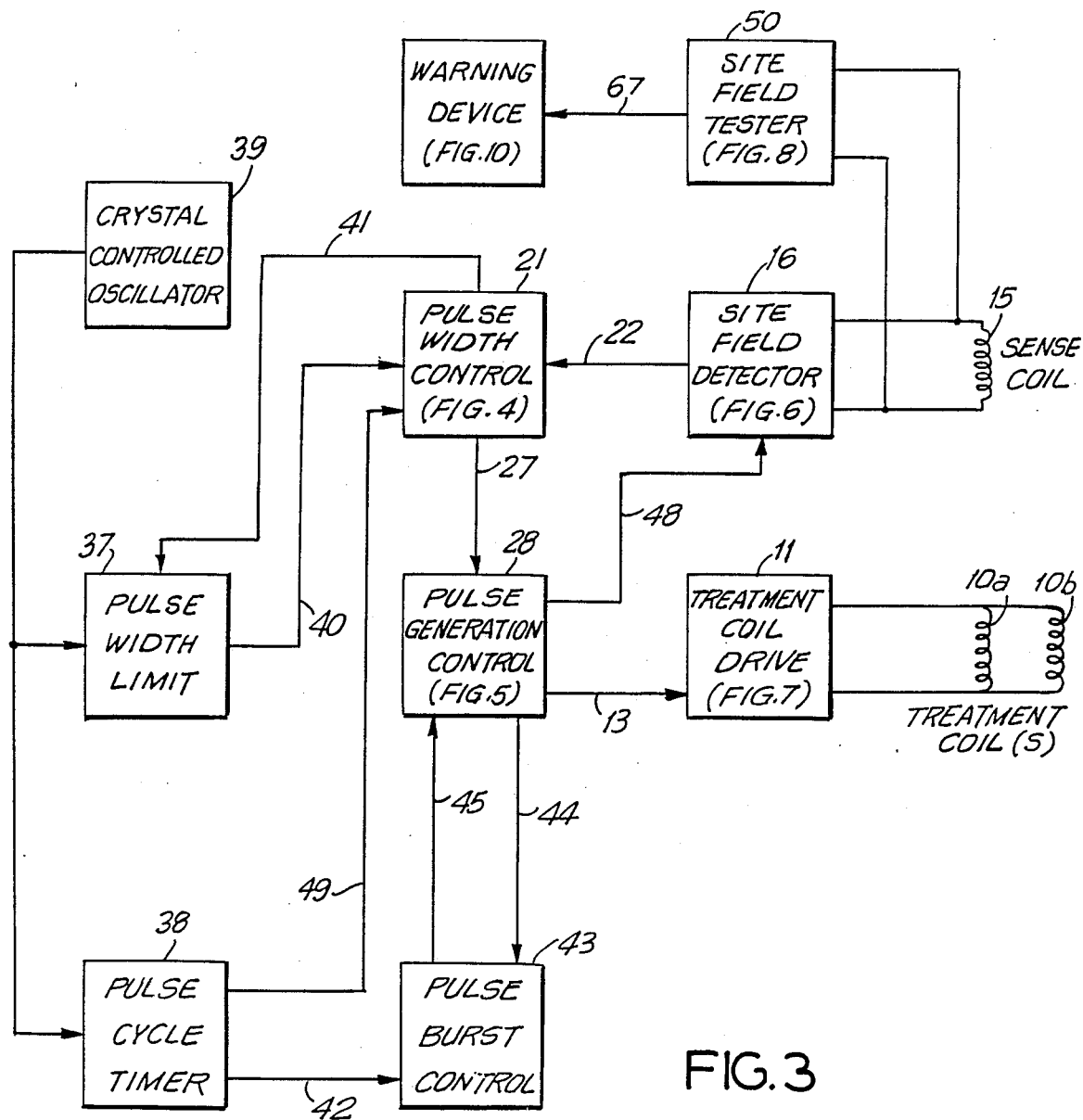
FIG.3

APPARATUS FOR REACTIVELY APPLYING ELECTRICAL ENERGY PULSES TO A LIVING BODY

RELATED APPLICATIONS

This is a continuation-in-part of application Ser. No. 943,542, filed Dec. 17, 1986, now abandoned, which is a division of application Ser. No. 591,476, filed Mar. 20, 1984, now U.S. Pat. No. 4,654,574, which is a division of Ser. No. 509,830, filed June 29, 1983, now abandoned.

FIELD OF THE INVENTION

This invention is in the general field of electronic medical devices but, more specifically, is directed toward the field of devices which apply electrical energy impulses to the body and which reactively induce electrical currents and voltages at the directed site within the body to provide therapeutic treatment of cells and tissues within the body to stimulate growth or repair bone structure with the body.

DESCRIPTION OF THE PRIOR ART

The prior art is best exemplified by the following U.S. Pat. Nos. Manning 3,893,462 dated July 8, 1975; Ryaby, et al. 4,105,017 dated Aug. 8, 1978; Ryaby, et al. 4,266,532 dated May 12, 1981; and Ryaby, et al. 4,266,533 dated May 12, 1981. All three of the Ryaby, et al. patents are offsprings of a common parent application and in substance deal essentially with a single device so they can be considered and treated as one.

These prior art patents describe the history and background of the development of the electronic medical devices with which the instant invention is concerned so there is no need to repeat that same information here. These prior art patents as well as published papers, some of which are referred to in the prior art patents and some of which are cited in the file histories of the prior art patents, describe the theories, the experiments and the tests which, over the years, have lead to the development of the electronic medical therapeutic devices such as the instant invention. These same prior art patents discuss the theories explaining or describing the phenomenon of cell and tissue repair by the application of controlled pulses of electrical energy whereby bone healing has been stimulated. Further, these same prior art patents detail and document, where available, the features and advantages of applying pulses of electrical energy to the site under repair by external means rather than by use of implanted electrodes. To the degree that these descriptions and explanations are not purely speculative and have acceptable scientific foundation applicants accept those propositions so find no need to repeat the same propositions here. Suffice as to point out that applicants have experimentally determined that the therapeutic devices of the nature described herein have provided and are providing beneficial results.

SUMMARY OF THE INVENTION

A transducer, which may be a treatment coil is arranged to receive pulses of electrical current and to develop a field and, in this embodiment, to apply the field in the form of magnetic pulses onto the site being treated in a living body in the usual and well-known fashion. The electromagnetic energy induces voltages and currents at the body site which therapeutically act on the cells and tissues to aid in healing of bone structure at the treatment site. A sensor is coupled to the transducer to detect the developed field and to produce a signal which can be used to control the developed field. In the described embodiment a sensing coil is electromagnetically coupled to the treatment coil to pick up signals representative of the developed field. Electrical current from an originating energy source such as a DC voltage source sometimes referred to as B+ is fed to the treatment coil by a coil drive circuit which essentially comprises an electronic switching device in series with B+ which is turned on and off at a prescribed rate to control the repetition rate of the applied pulses as well as the width and the pulse duty cycle. The signal picked up by the sensing coil fed to a circuit for controlling the developed field. This is done by integrating the sense coil signal and comparing it to a prescribed magnitude and when it reaches that magnitude it momentarily turns off the coil drive circuit to terminate the pulse and collapse the developed field. After a short interval, the coil drive circuit is re-energized and the process is repeated. The pulse width and developed field is controlled in this fashion so that the peak of the field applied to the site remains relatively constant. If the peak should tend to increase due, for example, to the treatment coils moving closer together, the pulse width will automatically decrease so that the peak of the applied field will be virtually unchanged. If the applied field energy should tend to decrease due, for example to a drop in the B+ level or circuit deterioration, this will be automatically compensated for by an increase in the pulse width.

Further associated with the coil drive circuit control is a first counter which counts the number of applied treatment pulses produced by the coil drive circuit and when that number reaches a prescribed quantity, generation of additional coil drive pulses is blocked. This provides a burst cycle of a burst of a prescribed number of pulses followed by a rest period. Another counter is utilized to control the restart of the pulse cycle, that is, the time at which the rest period ends and the pulse burst is restarted. At the end of the rest period as determined by the second counter, the first counter is reset and another burst of pulses is initiated.

As an added feature a third counter is provided to insure that the width of the applied pulse does not exceed a prescribed limit. In the event that the integrator-comparator circuit which responds to the sense coil signal operates to permit a pulse width greater than an acceptable limit, the third counter produces a trigger signal which is used to momentarily turn off the coil drive instead of the integrator-comparator circuit which would normally turn off the coil drive pulse. This is a safety factor to insure that pulse width stays within a desired limit.

Another feature is a further circuit coupled to receive a signal from the sense coil and to test that signal to make sure that the developed field is of sufficient energy level to produce the desired therapeutic results. In the event the developed field is determined to be below the desired energy level, the testing circuit activates a warning device.

Yet another feature is provided by a circuit having an additional winding which is electromagnetically coupled to the treatment coils to restore to the originating energy source some of the energy of the treatment coil which otherwise would be wasted. The signal induced into the additional winding is fed back into the B+ energy source for the device thereby conserving a substantial amount of energy which would otherwise be lost.

DESCRIPTION OF THE DRAWINGS

FIG. 1 illustrates the general appearance of a burst cycle used in a preferred embodiment of the invention;

FIG. 2 is an enlarged illustration to show more detail of a somewhat idealized form o the pulses applied to the treatment site;

FIG. 3 is a block diagram of an embodiment of the invention in which the device is arbitrarily divided up circuitwise into convenient functional sections;

DESCRIPTION OF THE PREFERRED EMBODIMENT

While it has been determined that there are certain requirements for the pulse width, the pulse repetition rate and the rest period between pulse bursts, which might be called the burst duty cycle, these are not a part of or considered to be novel aspects of the instant invention. The pulses which are described herein and are illustrated in FIGS. 1 and 2 are for illustrative purposes only in order to explain the operation of the device. Typically, as shown in FIG. 1, a burst of about one-hundred or so pulses should occur during each burst cycle which, in this example, is 660 milliseconds long. The width of each drive or forward pulse 1 as illustrated in FIG. 2, may range from about 200 to 300 microseconds with a 30 microsecond pause or interval 2 between pulses during which the developed field declines. In this example a pulse width of 270 microseconds was chosen, therefore, the burst of one hundred pulses takes 30 milliseconds so there is a 630 millisecond rest period between bursts. It should be understood that the pulse forms illustrated in FIGS. 1 and 2 are intended to merely represent the pulses produced by the device and are somewhat idealized and are used only to assist in describing the operation of the device. Also, the numbers used herein, while likely to be close to those used in certain commercial applications of the therapeutic devices incorporating the instant invention, are not intended to limit the invention to these numbers nor is there anything considered to be unique about these numbers as related to the instant patent application. The drive pulse 1 can be considered to be in the positive direction and during the interval 2 in which the field there is a negative going pulse. As will be described later, this negative going pulse is clamped.

Figure 7:
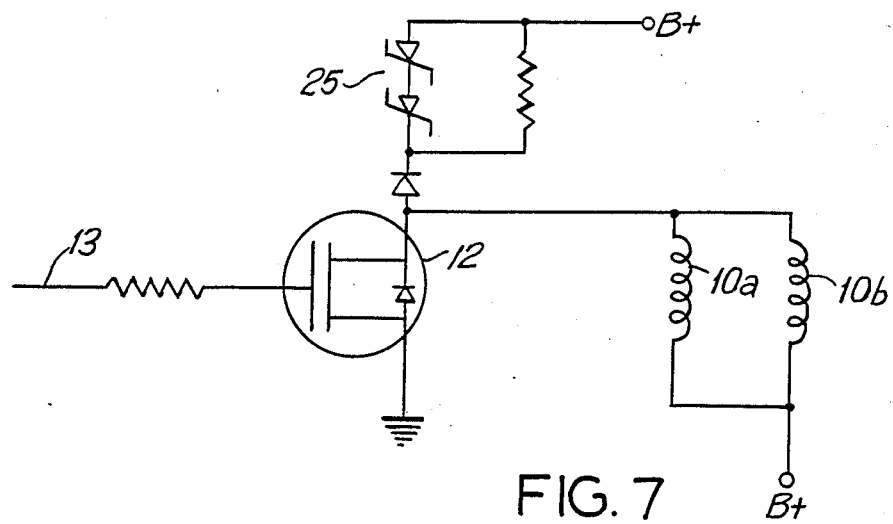
FIG. 7 is a diagram of the treatment coil, and drive circuitry.

In the embodiment to be described first, the drive pulses are applied by two treatment coils 10A and 10B which are electrically in parallel but which generally are physically separated from one another with the treatment site located somewhere in between. This is conventional. Electrical current is fed to the treatment coils by the coil drive circuit 11 (FIG. 3) by electrically turning on and off an electronic switch 12 (FIG. 7) by a signal which is applied to line 13 which is connected through a resistor to the control element of electronic switching device 12. When the signal applied to line 13 is of the correct magnitude and polarity, switch 12 is turned on so that current flows through coils 10A and 10B from an originating DC energy source (identified in the various drawings as B+) through switch 12 to produce a forward or drive pulse 1 (FIG. 2). To end the pulse a suitable signal on line 13 terminates the conduction of switch 12 so no further current flows through coils 10A and 10B except for that induced by self-induction of the coil windings as the magnetic field declines. This is the interval 2 between each of the drive pulses during which the pulse and field declines or collapses.

Figure 4:
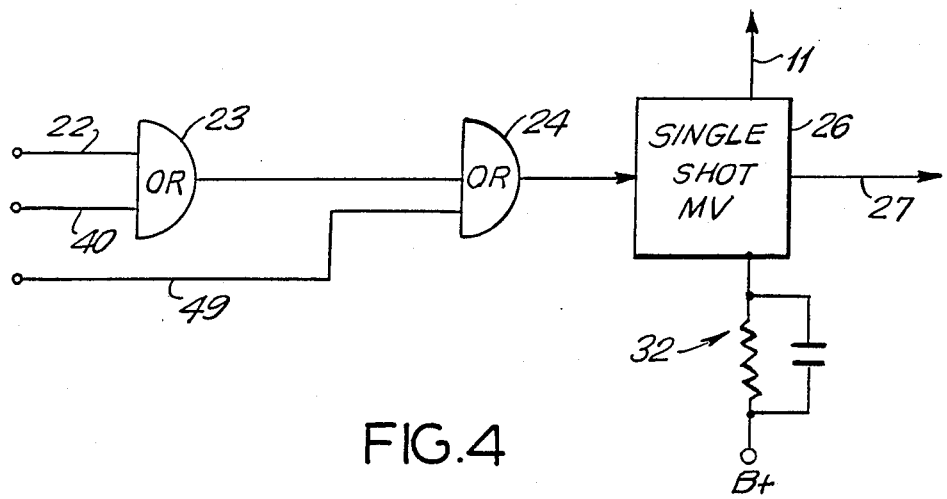
FIG. 4 is a part of the circuitry which is utilized for controlling the developed field by controlling the pulse width and which is identified in FIG. 3 as pulse width control.
Figure 5:
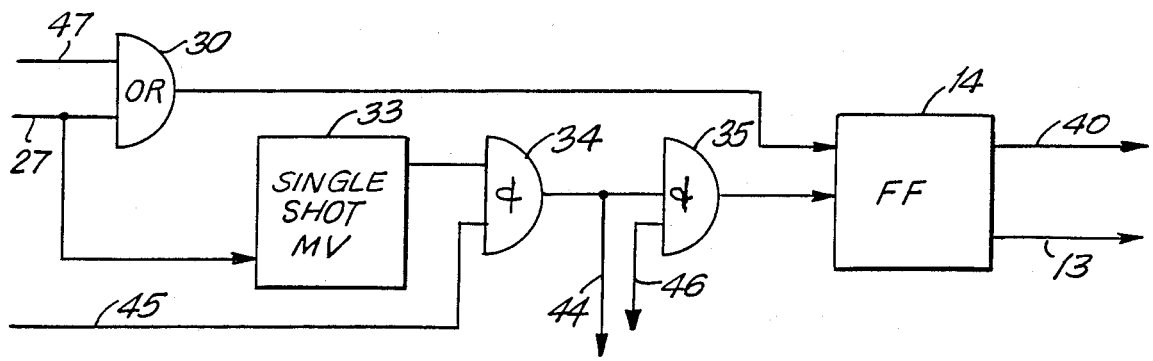
FIG. 5 is a diagram of another part of the circuitry for controlling the production of the pulses and which is identified in FIG. 3 as pulse generation control.

The signal on line 13 which controls the operation of switch 12 comes from an output of a bistable flip-flop 14 in the pulse generation control circuit (FIG. 5). Assuming at first that flip-flop 14 is set to a condition to provide a signal to turn on switch 12, a magnetic field is developed by treatment coils 10A and 10B which is detected by a sensor in the form of coil 15. The output of coil 15 after any necessary appropriate signal conditioning can be used to control the developed field in a variety of ways. One way is to control the width of the drive pulse to achieve a desired level of peak field. In the instant embodiment the signal from coil 15 is fed to the input of site field detector 16. The signal appears as n input to integrator 17 (FIG. 6) whose output appears across a series combination of variable resistor 18 and fixed resistor 19. The arm of variable resistor 18 carries the proportionate signal output from integrator 17 as an input to comparator circuit 20. The integrator 17 works in the conventional fashion of taking the general signal received from sensing coil 15 which is of a general square wave form and integrating it to produce a ramped voltage output. When the output voltage reaches a magnitude level as determined by the setting of the variable resistor 18, comparator 20 produces an output signal which is fed to the pulse width control circuit 21 through line 22 (FIG. 4). In the pulse width control circuit this signal is combined in a logical OR circuit 23 whose output is an input to another OR circuit 24. Neglecting for the moment the other input to OR 24, the signal from OR 23 passes through OR 24 and provides a signal input to a one shot or single state multivibrator 26. The latter operates in a conventional fashion such that the leading edge of a signal applied to it produces an immediate output on line 27 which is then fed to the pulse generation control circuit 28 (FIG. 5)

where it passes through OR 30 to flip-flop 14 to switch flip-flop 14 to a stable state which removes the signal from line 13 thereby closing switch 12 to terminate the electrical pulse to the treatment coils 10A and 10B.

Referring back to the pulse width control circuit of FIG. 4, the one shot multivibrator 26 operates in a conventional fashion to hold its switched-to condition only temporarily for a period of time controlled by the time constant of the RC circuit combination 32. In this case, as an example, the hold time is about 30 microseconds. When that time expires the one-shot 26 reverts back to its original stable state The dropping off of the signal output from one- shot 26 occurs on line 27 to remove the signal input to OR 30 and causes single-shot multivibrator 33 to produce an output signal which is fed as an input to AND 34. Assuming for the moment that the gating input to AND 34 is present, a signal will appear at the input to AND 34 (the purpose of which will be described later) and as another input to flip-flop 14 to reset it back to its other stable state to once again produce an output signal on line 13 with a resultant drive pulse input by the treatment coils 10A and 10B. In essence what has been described to this point is the manner in which the pulses illustrated in FIG. 2 are produced. The leading edge of the pulse occurs when flip-flop 14 is in one stable condition to produce an output signal at 33 and the pulse remains until integrator-comparator circuit in the site field detector 16 produces a signal to change the state of flip-flop 14. Flip-flop 14 remains in this condition and the drive pulse is terminated for an interval set by the time constant of the RC circuit 32 in pulse width control 21. As a result, if the field generated by treatment coil 10 should tend to decrease due to a deterioration of a component in the treatment coil drive circuit, for example, this would result in the signal from the sense coil 15 taking longer to reach the preset level at comparator 20 thereby resulting in extending the time that switch 12 remains on thereby producing a wider pulse to bring the applied field back up. Similarly, mutatis mutandi, if the field produced by the treatment coil should tend to increase.

Referring back to FIG. 3, the pulse width limit 37 and the burst cycle timer 38 are conventional digital electronic counters, which are incremented by electrical pulse inputs from a conventional crystal controlled oscillator 39. Since the counters are conventional, selection from a variety of commercially available types is merely a matter of choice and can be made by one of ordinary skill in the art so no detail of the construction or operation of these devices is felt to be necessary. Similar with the crystal controlled oscillator 39. Pulse width limit 37 is a counter constructed to produce an output signal on its output line 40 once for every predetermined period of time. In this case the time period is 300 microseconds. This output serves as an input to pulse width control 21 as the second input to OR 23 (FIG. 4). As stated earlier, if the other input to OR 23 coming from terminal 22 does not occur within 300 microseconds after the start of the pulse in order to terminate the drive pulse, then the input on line 40 will occur and will pass through OR 24 to one-shot multivibrator 26 to terminate the pulse at 300 microseconds. Output 41 from multivibrator 26 is fed back to pulse width limit 37 to reset it to zero. So each time the drive pulse is terminated whether by virtue of the input from line 22 or by a signal on line 40 into OR 23, pulse width limit counter 37 is reset to zero and starts a new sequence of operation to count up to a maximum of 300 microseconds.

Burst cycle timer 38 is constructed to produce a signal output once every prescribed period of time which in this case is 660 milliseconds. A output from burst cycle timer 38 on line 49 is fed to the pulse width control 21 and then to the pulse generation control 28 to synchronize the start of the burst cycles with the start of the pulse width limit 37 and the pulse burst control 43. Another output on line 42 serves as an input to pulse burst control 43 which is also another conventional counter which is set to a prescribed count level by an input on line 42. The second input to pulse burst control 43 is on line 44 and each time a signal or pulse occurs on that line the counter counts down or is decremented. In the present example the input on line 42 sets pulse burst control 43 to a count of one-hundred and the signal pulses on line 44 count this down until it reaches zero. When the latter occurs a signal exits on line 45 as an input to the pulse generation control 28. This provides the gating input to AND 34 (FIG. 5). As long as pulse burst control 43 is other than zero, a gating signal is present on line 45 and drive pulses with intermediate reverse field intervals are repeatedly generated by the action of flip-flop 14 in the manner described previously. When the content of pulse burst control 43 reaches zero, the signal from multivibrator 33 is not gated through AND 34 to set flip-flop 14 to the condition to generate a pulse. This is the start of the 630 millisecond rest period between pulse bursts as illustrated in FIG. 1. After the 630 millisecond rest period, burst cycle timer 38 produces an output on lines 42 and 49 which then restarts pulse generation and resets pulse burst control counter 43 to its count level of 100 and a burst of 100 drive pulses is again generated in the manner as described earlier. Line 44 comes from the output side of AND 34 and provides the signal which is carried back to pulse bust control 43 to reduce its count by one each time a pulse is generated.

Referring back to FIG. 5 the signal to AND 35 on line 46 is a signal indication of the condition of the DC (B+) energy level of the device. If the energy level is acceptable, a suitable circuit, not shown, produces a signal which keeps AND 35 gated on. If the energy level falls below an acceptable limit, the generation of pulses is blocked at AND 35. It has been found that if the energy level is too low, the applied pulses lose their therapeutic effect. The circuit for testing the DC energy level for the acceptable value is not considered part of the instant invention and so will not be described.

Still with reference to FIG. 5 a second input to OR 30 at 47 is a power up clear input. This ensures that flip-flop is set to a state to keep switch 12 open when power is first applied to the device so no current is fed to treatment coil 10 before the power is fully up.

Figure 6:
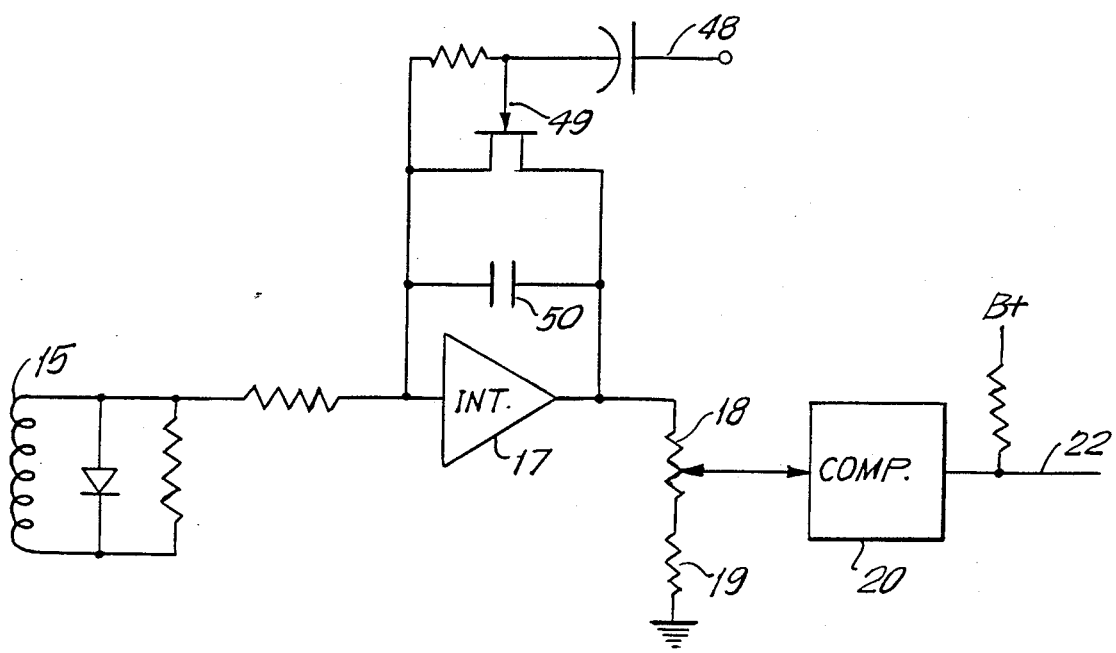
FIG. 6 is a diagram of another part of the circuitry for controlling the pulse width comprising the integrator-comparator which combination is identified in FIG. 3 as site field detector.

Also with respect to FIGS. 5 and 6 an output 48 from flip-flop 14 is fed back to the integrator circuit of FIG. 6 through a capacitive coupling to reset integrator 17 each time a pulse is terminated. This reset gets the integrator ready to respond to the next treatment pulse which is picked up by the sensing coil 15. In essence this reset signal on line 48 momentarily energizes electronic switch 49 to allow capacitor 50 to discharge rapidly and thereby set the integrator circuit to a condition ready to accept the next input pulse from the sensor.

Figure 8:
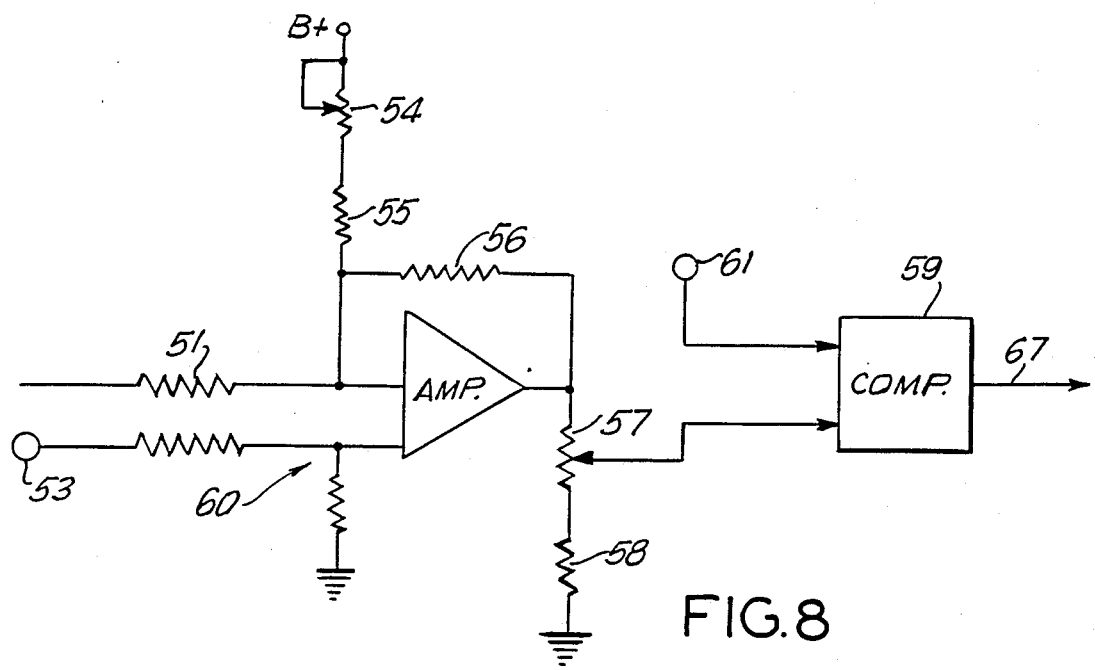
FIG. 8 is a diagram of the circuitry for the site field tester.

A site field tester 50 is connected electrically in parallel with site field detector 16 across the sense coil 15. Referring to FIG. 8, the signal induced in sense coil 15 is coupled through resistor 51 to an input to amplifier 52. Connected as another input to amplifier 52 is a bias voltage which is tapped off a voltage divider network 60 connected to a voltage reference source 53. The DC energy source, B+, is connected through the series arrangement of potentiometer 54 and fixed resistor 55 to the same input of amplifier 52 as the signal from sense coil 15. A feed back resistor 56 is connected from the output of amplifier 52 back to the same signal input. The bias voltage from the source 53 is to set the operation state of the amplifier 52 so that the sense signal input does not drive it into saturation. The function of the circuitry connecting B+ to amplifier 52 and resistor 56 is to prevent variations in the level of the B+ voltage from affecting the operation of the site field tester. Another circuit, not shown and not considered to be a part of the instant invention, is included to give an alarm if the B+ voltage level should fall below an acceptable magnitude. The purpose of the site field tester 50 is to give a warning if the pulses are not applying suitable energy to the treatment site for various reasons such as: (a) the treatment coils (if more than one) being too far apart; (b) failure of or in a treatment coil; (c) loss or deterioration of a component in the treatment coil drive circuit, etc. If the pulse inadequacy is due to a drop in the level or magnitude or the B+ voltage this will be detected and signalled by another circuit, not shown. It is important that any variations in the B+ voltage level which might tend to change the energy level of the developed field applied to the site be balanced out in the site field tester.

Amplifier 52 operates in a conventional fashion and its output is developed across a pair of resistors 57 and 58. Part of the output is tapped off variable resistor 57 and is fed as an input to comparator 59. The other input to comparator 59 is from a preselected voltage level to which the signal output from amplifier 52 is being compared to determine whether the developed field, as represented by the sensed signal, is of suitable and acceptable magnitude. The output of comparator 59 is used to produce an audible or visual (or both) signal or alarm indication that the developed field applied to the site is below an acceptable energy level in a manner to be described later.

The setting of potentiometer 54 for the proper balancing out of the effect of the B+ is generally done by trial and error but may be calculated. When two treatment coils are used the appropriate and acceptable energy level for the applied pulse is set by first separating the treatment coils a prescribed distance, for example by about five inches Potentiometer 57 is then set so that the output of comparator 59 is just enough to give a signal indication of inadequate pulse energy level If thereafter the distance between the coils should be five inches or more a signal indication would then be generated. Other types of the aforementioned failures which result in substantial loss in pulse energy level would cause a similar indication. The concept here is that a signal indication should be given when the pulse energy level falls below a prescribed amount otherwise the treatment would be continued under the mistaken belief that therapeutic benefits are being achieved.

Figure 9:
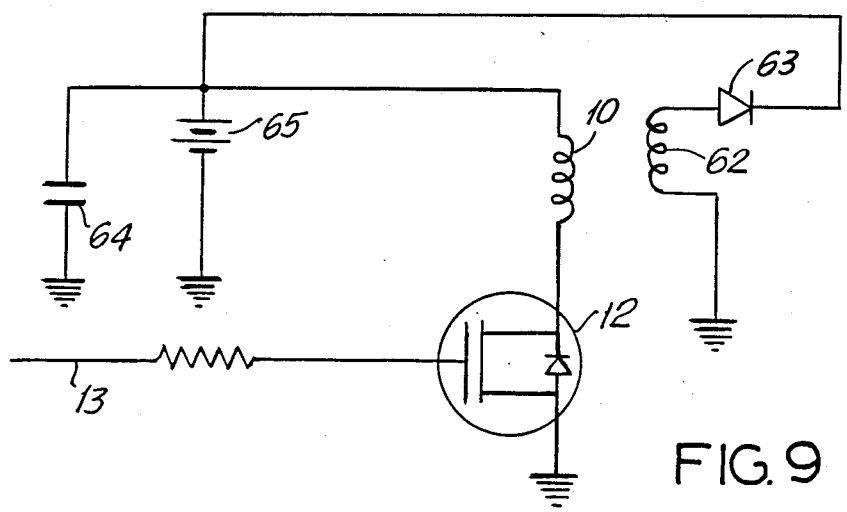
FIG. 9 is a diagram of an alternate coil drive circuit which includes energy restoring circuitry.

Another feature of the invention is provided by an alternate coil drive circuit which includes an energy restoring circuit as illustrated in FIG. 9. An energy retrieving coil 62 is inductively coupled to a treatment coil 10. The voltage induced in coil 62 by the decline of the magnetic field during the interval between dive pulses is rectified through a diode 63 and is fed back to charge capacitor 64 which is electrically in parallel with the B+ battery source 65. In this fashion then the energy which would otherwise be lost is at least partly recovered by being used to recharge the B+ source and thereby restores what otherwise would be wasted energy The energy restoring circuit of FIG. 9 provides the additional benefit of a substantially constant forward to reverse voltage ratio over a range of DC source voltages (B+) The circuit of FIG. 7 produces a variation of forward to reverse voltage ratio as the DC source voltage varies. The reason is that in the circuit of FIG. 9 the DC source voltage is used for both the forward or drive pulse and for the clamp during the interval between drive pulses. The circuit of FIG. 7 uses the DC source voltage B+ for the forward or drive pulse and the zener diodes (25 in FIG. 7) voltage for the clamp or reverse voltage during the interval between drive pulses.

Another advantageous energy recovery feature is the sequential charging and discharging of a storage capacitor to assist the battery supply. The storage ability of a capacitor is electrostatic in nature, whereas the battery is electrochemical. A battery is generally more advantageous in supplying a larger energy requirement over a longer period of time. A battery is generally less advantageous in rapidly providing and accepting energy when compared to a capacitor. This difference in time-energy capabilities is due to the electrochemical reaction which occurs during the battery cycle. Also, it is generally advantageous if the battery is a low voltage device to minimize the number of cells in series although the device operating voltage is optimized at another level which can be considerably higher.

Consequently, it may be advantageous if, during some or all portions of the operation cycle, energy would be recovered from and stored in a storage capacitor. Examples of these circuits maybe seen in FIGS. 14 through 16 which are alternate coil drive circuits that include an energy restoring feature.

Figure 14:
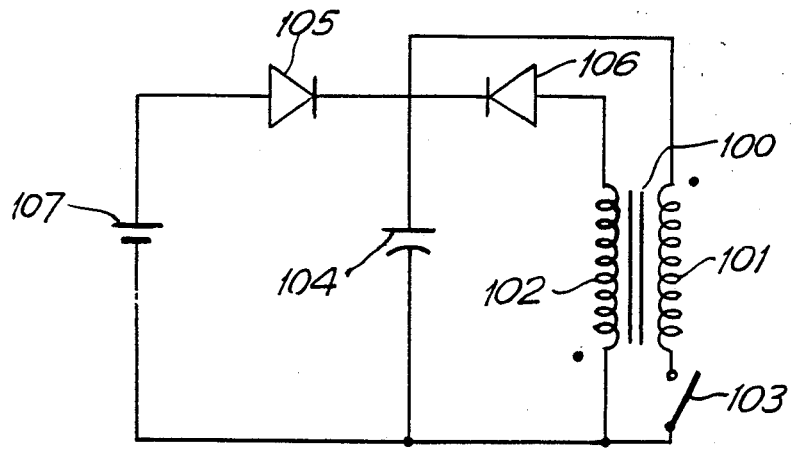
FIGS. 14, 15 and 16 show alternative embodiments of coil driver circuit which include an energy storage and recovery capacitor.

In FIG. 14, a PEMF transducer includes an energy retrieving coil 102 having an iron core 100 inductively coupled to a treatment coil 101 which is connected to a switch 103. The energy retrieving coil 102 utilizes a diode 106 to rectify pulses to a storage capacitor 104. A battery 107, with rectifying diode 105, is placed across the treatment coil 101. FIG. 14, as well as FIGS. 15 and 16, shows an iron core treatment transducer for illustrative purposes although air core transducers may also be utilized in an appropriate circuit.

In operation, the battery 107 of FIG. 14 provides a pulse to treatment coil 101 when switch 103 is closed. A voltage is induced in energy retrieving coil 62 by the decline of the magnetic field which begins when switch 103 is opened. Diode 105 blocks these pulses from returning to the battery 107. Thus, in different portions of the operating cycle, the battery furnishes energy to the treatment coil 100, and coil 102 recovers the field energy and charges storage capacitor 104. Capacitor 104 subsequently furnishes energy back to the treatment coil, thereby lessening the net drain on battery 107. Thus, the steps are (1) establish the field from the battery energy, (2) recover energy from the field and furnish recovered energy to a storage capacitor, (3) remove energy from the storage capacitor to create the magnetic field in the treatment coil space, and (4) recover energy from the declining field and return this energy to the capacitor. An optional dormant period or periods may be included in the cycle.

Figure 15:
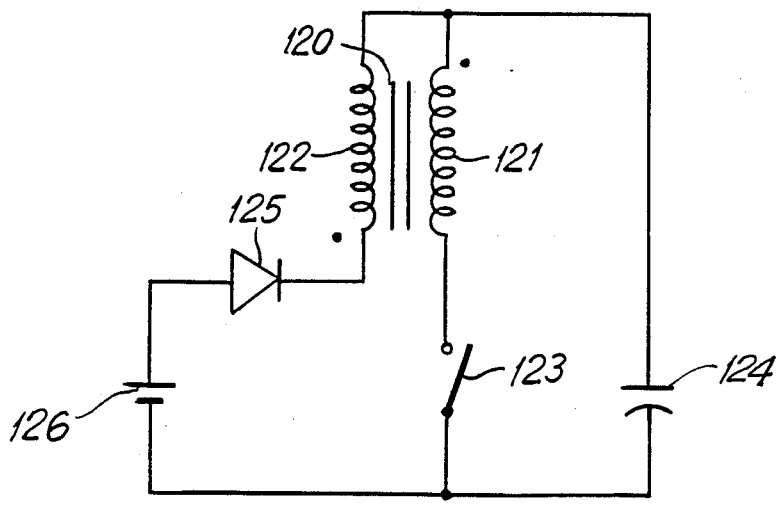
Figure 16:
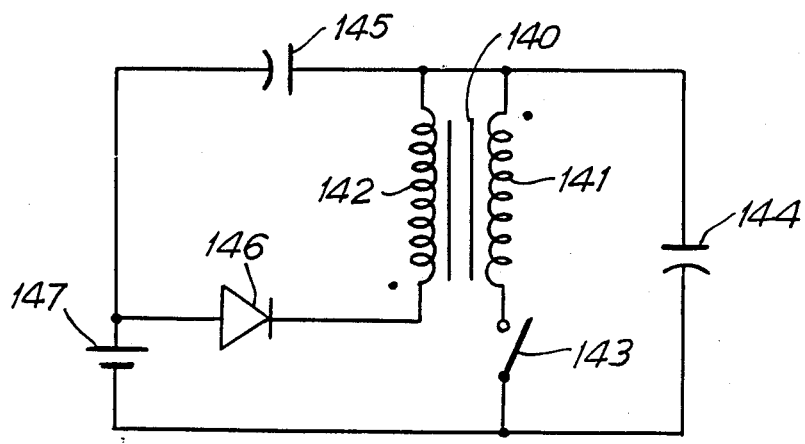

Another embodiment of the energy saving circuit is shown in FIG. 15. In FIG. 15 a treatment coil 121 having an iron core 120 is inductively coupled to an energy recovery coil 122. The coil 121 is connected to a solid state switch 123. A storage capacitor 124 is placed across the series combination of coil 121 and switch 123. A battery 126 and rectifying diode 125 are connected to the treatment coil 122.

When operating, this circuit withdraws current from capacitor 124 during the buildup of the magnetic field. The current from battery 126 is supplied at a lower voltage than is maintained on capacitor 124 and is only used to recharge the capacitor 124 and not to produce an output pulse. Current is only supplied to the treatment coil 121 when switch 123 is closed, and thus current only flows from capacitor 124 during this interval. When switch 123 is opened, energy from the battery recharges capacitor 124 aided by the voltage induced in energy recovery winding 122. In this circuit, the capacitor voltage is approximately two and a half times higher than the battery voltage and depends upon the efficiency of the energy recovery process.

A variation of the circuit depicted in FIG. 15 is shown in FIG. 16. FIG. 16 is similar to the circuit of FIG. 15 and has corresponding components. Thus, the FIG. 16 circuit has a treatment coil 141 having an iron core 140 inductively coupled to an energy recovery coil 142 which is connected to solid state switch 143. Storage capacitor 144 is placed across coil 141 and switch 143. A battery 147 is connected to coil 142 through rectifying diode 146. This circuit differs primarily from the one shown in FIG. 15 by the addition of capacitor 145. This additional capacitor 145 provides a better duty cycle, lower current peaks and improved crest factor.

In the circuit of FIG. 16, current is drawn from battery 147 during the charge and discharge portions of the operating cycle but not during the dormant period, if one is utilized. When switch 143 is closed, current is drawn from capacitor 144 in a manner similar to that of FIG. 15. As current is drawn from capacitor 144, the voltage drops. As current is drawn from both capacitors, current through capacitor 145 is furnished by battery 147. This circuit thus provides a more favorable duty cycle in drawing current pulses from battery 147 and smaller current peaks than the circuit of FIG. 15. In each case in FIGS. 14–16, solid state switches 103, 123 and 143 are activated by appropriate logic circuitry known to the art.

Figure 10:
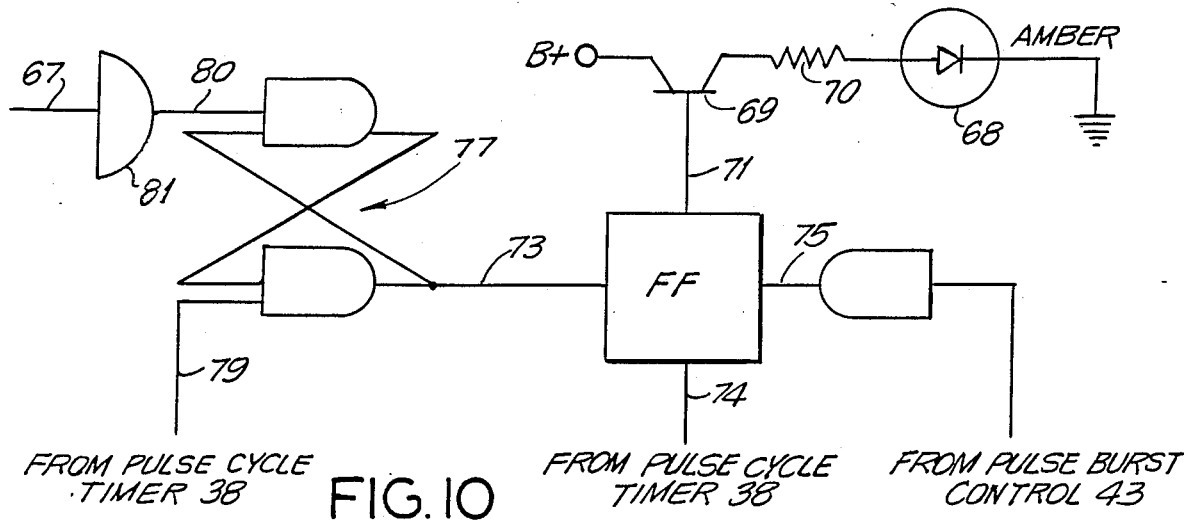
FIG. 10 is a diagram of the circuitry for giving a visual indication of inadequate pulse strength.

A circuit which provides a visual indication of inadequate pulse strength is shown in FIG. 10 and operates to energize amber light 68, which may be a light emitting diode (LED), when the pulse strength is inadequate. Preferably, each burst of pulses is separately tested for inadequacy. The circuit operate to turn off the LED during the burst time and if the burst of pulses is tested and found to be inadequate then at the end of the burst time the amber light is energized. This continues so the LED flashes on and off as long as the pulses continue to be inadequate.

LED 68 is in series with a transistor 69 and a current limiting resistor 70 to DC energy source B+. The operation of transistor 69 is controlled by output 71 from a bistable flip-flop 72. Flip-flop 72 has a set input at 73, a reset input at 74 and a readout input at 75. The signal to readout input 75 comes through an inverter 76. The set input 73 comes from an output from another bistable flip-flop 77 formed by a pair of inverters which are cross coupled in a conventional fashion. The signal to reset input 74 comes from pulse cycle timer 38 and, as described earlier, is a pulse which occurs once every 660 milliseconds. The signal to inverter 76 comes from the pulse burst control 43 and occurs when the latter reaches zero after being counted down from 100. This signal denotes the termination of the pulse burst and the start of the rest period.

One input to flip-flop 77 on line 79 also comes from burst cycle timer 38 and the other input to flip-flop 77 on line 80 comes through inverter 81 from the output of the site field tester 50.

In operation, a signal from burst cycle timer 38 at input 74 resets flip-flop 77 and on line 79 sets flip-flop 77. This is the same signal which is used to start the pulse cycle with a burst of pulses and sets the pulse burst control 43 to a count of 100. If any pulse, even if just a single one, in a burst is found to be adequate by site field tester 50, comparator 59 produces an output signal at 67 which is applied through inverter 81 to flip-flop 77 to reset it. This produces an output from flip-flop 77 which appears as an input at 73 to set flip-flop 72. At the end of a burst the signal from the pulse burst control 43 applied to flip-flop 72 through inverter 76 causes flip-flop 72 to be read out and since it is in the set position the readout is such that transistor 69 remains nonconductive and the LED 68 remains off. Everything remains status quo throughout the rest period. At the start of a new burst flip-flops 77 and 72 are set and reset again by pulse cycle timer 38 as described previously and another cycle is repeated. If during a burst not a single adequate pulse is detected, flip-flop 77 remains set. The resulting output sets flip-flop 72 so when the signal arrives from pulse burst control 43 at the close of the burst to readout flip-flop 72, transistor 69 is made conductive and LED 68 energizes and remains glowing through the remainder of the rest period. When flip-flop 72 is reset once again by pulse cycle timer 38 the LED will go off and will remain off unless the test of the next (or any later) burst of pulses finds no adequate pulse. If successive bursts are found to have no adequate pulses LED 68 will be repeatedly turned on and off.

Figure 11:
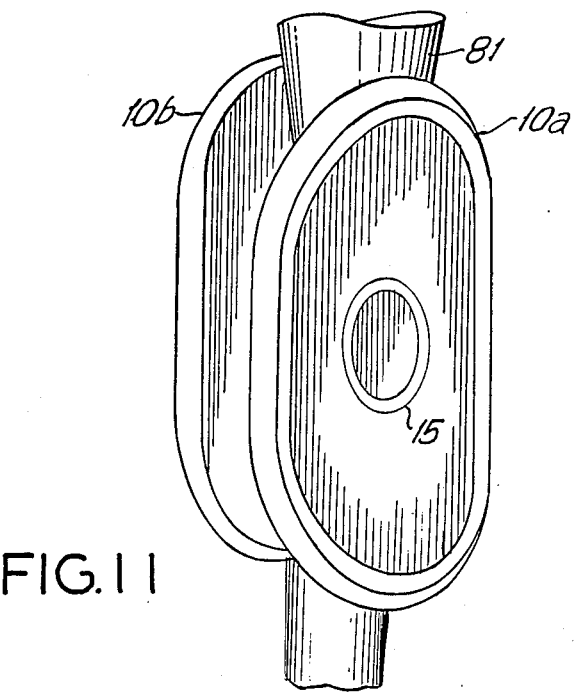
FIG. 11 illustrates a geometry of multiple treatment coils used in an embodiment of the invention.

FIG. 11 is intended to illustrate an embodiment of the invention utilizing two treatment coils to show the relative geometry and location of the treatment coils with respect to the site being treated. The treatment coils 10a and 10b may be wound circumferentially on the outer edge of their respective holders which might be made of plastic or some other suitable non-magnetic material. The coils are separated from one another with the site being treated, which in this case might typically be a bone in a limb, being located between the coils. The sense coil 15 which is substantially smaller than the treatment coils 10a and 10b is located substantially co-axially with one of the coils, 10a, on the same holder as the latter. Magnetic coupling between the coils and to the site is through air. Suitable electrical circuitry and a power pack for operating the device is contained in a housing, not shown, which is generally attached to the same holder as one of the treatment coils. When the treatment coils are properly located with respect to one another and the treatment site, they are generally then wrapped with some suitable material so they stay in position during the treatment. Preferably the power pack is a DC source so no electrical cords are needed which might interfere with the movement of the unit while it is being used. Generally the power pack is removable so that it can be removed for recharging and another power pack substituted so that treatment is uninterrupted. The amber light which is used to give a warning of inadequate pulse strength and any other visual and audible warning signals are generally also contained in the housing which contains the electrical circuitry. Of course it is necessary to run some electrical leads to the coil which does not have the power pack.

Figure 13A:
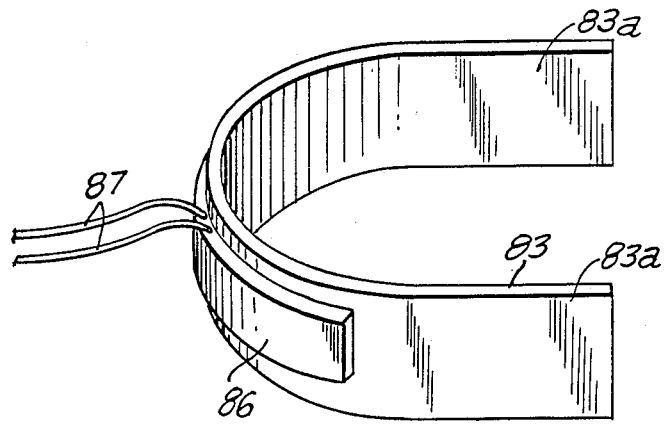
FIGS. 13A and 13B illustrate a single treatment coil employing a core and multiple energy restoring windings.
Figure 13B:
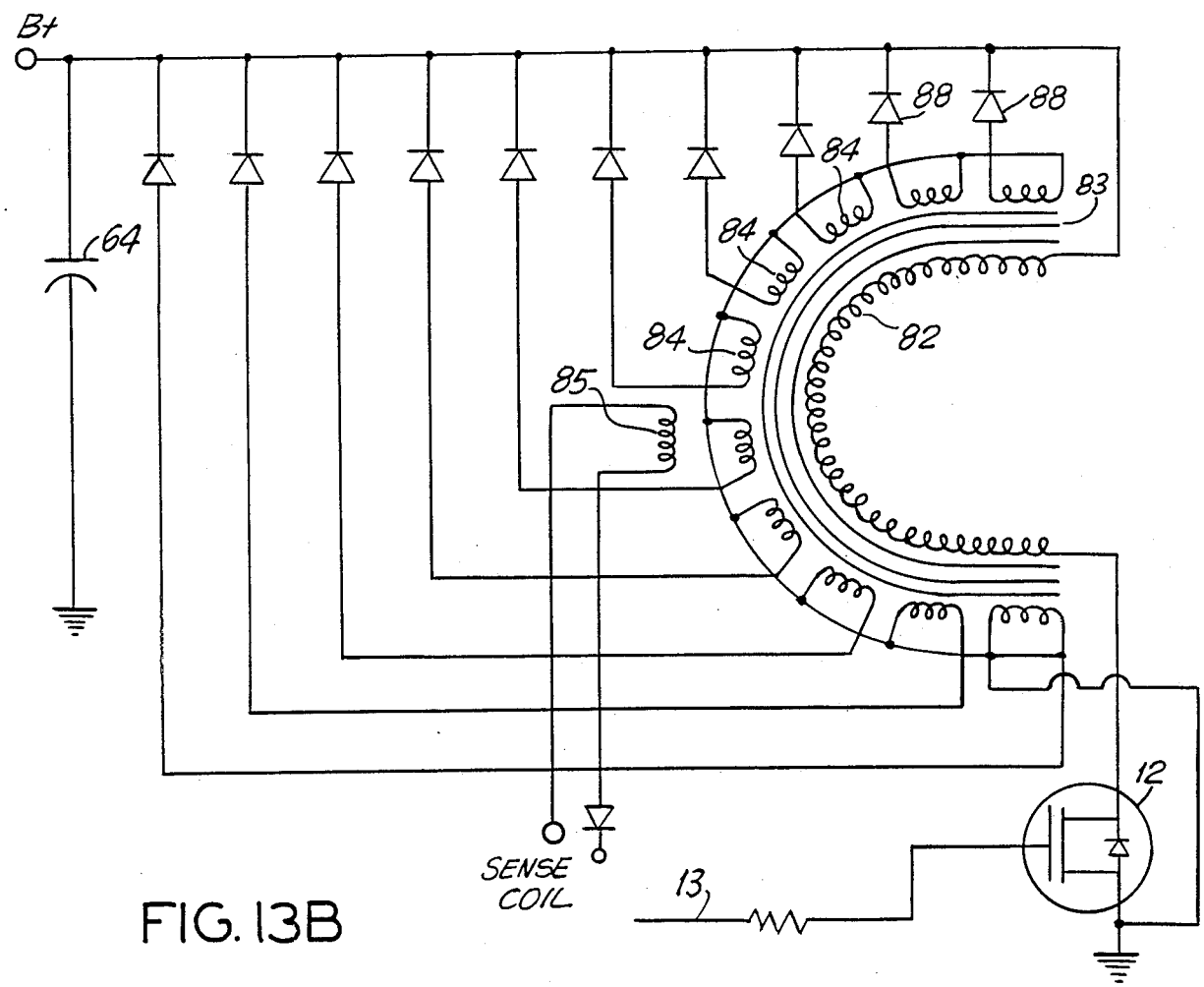

FIGS. 13A and 13B are intended to illustrate an embodiment of the invention utilizing a single treatment unit or coil. The treatment coil winding 82 is distributively wound on a U-core 83 of suitable permeable material and which is located at the treatment site. Multiple energy restoring windings 84 with associated diodes 88 are distributed in a somewhat uniform fashion around the perimeter of the U-core 83 to increase the efficiency of restoring energy during the collapse of the field, as described earlier. An additional coil 85 is wound around the core to sense the developed field. The coil is housed in a plastic or other suitable non-magnetic non-conducting material. It has been found that the FIG. 13 embodiment develops a substantially uniform field of suitable treatment magnitude in the region of the treatment site. Therefore, location of the treatment unit is not as critical as might otherwise be the case. Preferably the core is smoothly curved or arced at its closed end and the legs 83A of the U extend outward parallel to one another with their planar ends facing outward. The treatment site is generally centered between the legs 83A, inside the ends of the core and generally centered with respect to the height of the core. However, the design is such that, as stated before, the developed field is uniform within the region between the core legs 83A so that precise location is not that critical and greater flexibility for locating or placing the treatment site is permitted. An additional housing 85 holds the electronic circuitry and an electrical cord or cable 87 is provided.

Figure 12:
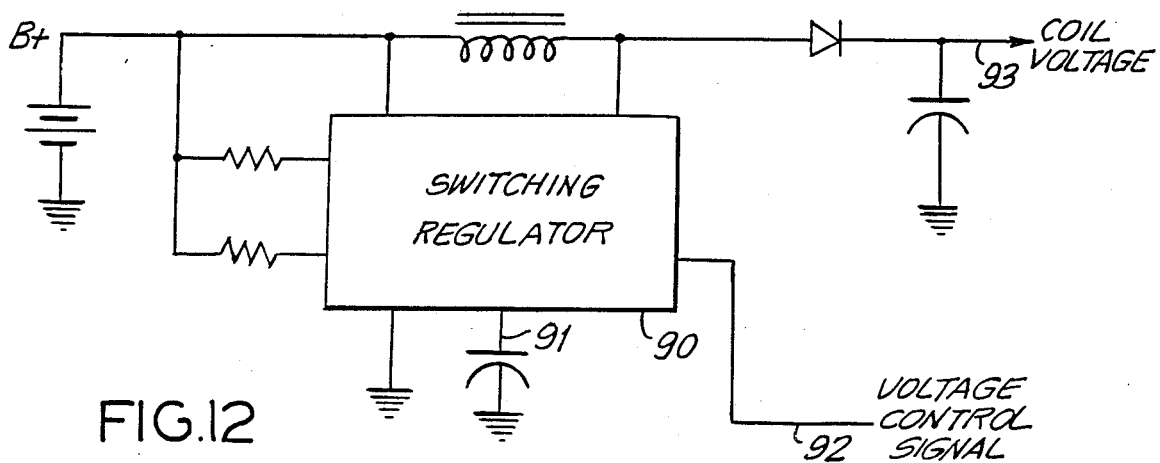
FIG. 12 is a diagram of a circuit for controlling the developed field by varying the voltage applied to the treatment coil.

The signal on the sense coil, which is representative of the developed field, can be used for additional or alternative purposes. For example, as illustrated in FIG. 12, it can be used to control the magnitude of the B+ voltage applied to the treatment coil. Switching regulator 90 is a device which is commercially available such as Raytheon's RC/RM 4193 Micro-Power Switching Regulator. It contains, inter alia, an adjustable free running oscillator and voltage comparator. The free running oscillator provides drive circuitry for a switch transistor. The oscillator frequency is determined by an attached external capacitor 91. When a signal from the sense coil, after any necessary processing, as applied to the voltage control signal input 92 falls below a predetermined level, the oscillations within the switching regulator 90 causes the output coil voltage at 93 to increase thereby bringing up the energy level of the developed pulse. If the sense coil signal and corresponding signal at 92 should increase above a predetermined level, oscillations in the switching regulator 90 cease which results in a decrease of the coil voltage at 93 and a corresponding reduction of the energy level of the developed pulse. If the circuit of FIG. 12 were used, it would replace the battery 65 of FIG. 9 or in FIG. 7 it would constitute the B+ line.

Alternatively two treatment coils with separate cores can be used. Each of the coils would be separately wound on its own core and the two cored coils arranged parallel to one another but spaced part. In general the treatment site would be placed between the two coils. In essence this would be similar to the coils wound on the legs of the U-core described above except that in this embodiment the cores would not be connected together. Preferably, the energy restoring windings with associated circuitry would also be used in this two core system.

I claim:

1. A device for reactively applying to a body site, a varying electrical energy field developed from originating energy source for stimulating repair or growth of tissue or bone structure in the body:

Means for developing a varying electrical energy field and for reactively applying said field to a body site;

Means for detecting the applied field and for producing a signal representative of the field;

Means responsive to said signal representation from said detecting means for controlling said field;

Electrical pulse generating circuit means coupled to said field applying means for feeding pulses of current to said field applying means for developing a pulsating field;

Said field controlling means comprising circuit means coupled to said pulse generating circuit means responsive to the signal from said detecting means for controlling the width of the current pulses; and Said circuit means for controlling the pulsed width includes an integrator circuit means coupled to said field detecting means for integrating the electrical signal from field detecting means, comparator circuit means coupled to the output of said integrator circuit means for producing an output signal when the integrator output reaches a prescribed level, and circuit means responsive to the comparator means output signal coupled to said current pulse generating circuit for terminating the current pulses.

* * * * *